United States Patent [19]

Keeling

[11] 4,271,148

[45] Jun. 2, 1981

[54] PROCESS FOR PREPARING LIVER FOR USE AS THERAPEUTIC AGENT

[76] Inventor: Walter W. Keeling, Roanoke & Market Sts., Amsterdam, Va. 24175

[21] Appl. No.: 78,890

[22] Filed: Sep. 25, 1979

Related U.S. Application Data

[63] Continuation-in-part of Ser. No. 956,395, Oct. 31, 1978, abandoned.

[51] Int. Cl.$^3$ .................. A61K 35/407; A61K 35/413
[52] U.S. Cl. .................................................... 424/106
[58] Field of Search .......................................... 424/106

[56] References Cited

U.S. PATENT DOCUMENTS

| | | | |
|---|---|---|---|
| 1,813,788 | 7/1931 | Walden | 424/106 |
| 1,914,338 | 6/1933 | Campbell | 424/106 |
| 2,032,544 | 3/1936 | McEllroy et al. | 424/106 |

FOREIGN PATENT DOCUMENTS

| | | | |
|---|---|---|---|
| 7722M | 3/1970 | France | 424/106 |

OTHER PUBLICATIONS

Spencer et al., Cancer Research, Part 2, vol. 25, No. 4, May 1965, p. 841, (No. 2858).

*Primary Examiner*—Jerome D. Goldberg
*Attorney, Agent, or Firm*—D. Paul Weaver

[57] ABSTRACT

An improved process for producing a palatable liver product having utility for use in treating certain blood diseases is disclosed. The process of the invention involves the reduction of the bulk of the liver without any loss of its essential components and comprises the steps of initially cooking the liver and thereafter subjecting the liver to a series of certain grinding and vacuum treatments. The resulting product may be encapsulated and/or pressed into tablets of a convenient size for human consumption. The processed liver may also be combined with a suitable binder and pressed into biscuit form. The liver product is very palatable, easily digested, and is particularly suitable.

6 Claims, No Drawings

PROCESS FOR PREPARING LIVER FOR USE AS THERAPEUTIC AGENT

RELATIONSHIP WITH CO-PENDING APPLICATIONS

The present application is a continuation-in-part of U.S. patent application, Ser. No. 956,395, filed Oct. 31, 1978, now abandoned.

BACKGROUND OF THE INVENTION

1. Field of the Invention

The present invention relates to the processing of liver and, more particularly, to an unique process for producing a palatable liver product.

2. Brief Description of the Prior Art

As known in the art, liver is one of the richest natural food sources of selenium as well as various other vitamins and nutrients. Liver is also known to be a major source of certain enzymes. Thus liver is a valuable and highly recommended foodstuff for individuals having a need or requirement for the nutrients provided by this product.

Although the statement of the problem is straight forward in practice, it has been found to be exceedingly difficult to control the intake of selenium, enzymes, etc., when same are ingested from the naturally occurring foodstuff themselves, i.e., liver or other foods such as various meats, fish, and the like.

In such a system it would be necessary to have the patient consume very large portions of the liver each day, i.e., on the order from 1 to 2 pounds, so as to obtain the required dosage and necessary intake of the enzymes and selenium. Obviously, many individuals do not have the appetite for, nor the capacity, to consume enough liver to benefit them in this fashion. It has also been discovered that in many cases, a sustained diet of liver is impossible to maintain because the patient cannot retain same in his stomach.

One possible approach to this difficult problem would be to reduce the bulk of the calves liver without losing any of its essential components. As should be apparent, the bulk of calves liver would have to be reduced to a quantity that would be acceptable to virtually any patient able to eat a minimal portion of solid food. To a large extent, attempted solutions and/or prior art proposals have involved extracting the liver with liquid extracts capable of removing the valuable components of the liver and either employing this extract in the form of a liquid or thereafter drying the extract to form a powdered product. Specific examples of such prior techniques are disclosed, e.g., in U.S. Pat. Nos. 1,813,788; 1,895,977; 1,914,338; and 2,032,544. While a number of such techniques have been made, none have proved to be entirely satisfactory. The present invention provides a remarkable solution to this long felt need of the prior art and overcomes the disadvantages of the prior art.

SUMMARY OF THE INVENTION

In summary, the present invention relates to the processing of liver in a manner so as to reduce the bulk of the liver without any loss of its essential components. In accordance with the present invention, the bulk of the liver is reduced to a quantity that is acceptable to virtually any inflicted patient who is able to eat even a minimal portion of solid food. It may be administered to individuals who are not afflicted with a disease but who desire to avail themselves of the inhibiting properties of the liver, and without having to eat large quantities of this meat daily.

In its broadest aspects, the process of the invention comprises the steps of cooking liver at a temperature of about 212° F., reducing this temperature to about 0° F.; subjecting the chilled liver to a first vacuum treatment and thereafter grinding the liver into rice-size granules, i.e., granules having an average length of about 5 to 20 millimeters. The granules are next subjected to a further vacuum treatment for an additional period of time and are further reduced in size, by grinding to a particle size approximating granulated sugar crystals. The finely divided liver particulates are finally subjected to a high vacuum on the order of about 20 to 28 inches of mercury, for a period of about 20 to 30 minutes. In a preferred embodiment the liver particulates may also be subjected to irradiation so as to produce a sterile and stable product.

The resulting product is ready for use and may, for example, be encapsulated and/or pressed into tablets of a convenient size for human consumption and in a form which does not require refrigeration or vacuum packaging to prevent deterioration. The processed granules, when combined with a suitable binder, may also be pressed into biscuit form to provide, in a single form, the required 200 to 300 micrograms daily supply of selenium and other nutrients. This product is very palatable and easily digested. The latter is opposed to the dense, unpleasant tasting liver product prepared by known processes.

From the above it is seen that the present invention provides a remarkable process for transforming liver into a light yet highly concentrated granular product, which may be added to other foods (such as sauces and/or gravies) without detection. As aforesaid, the product of the invention may also be compressed into biscuit form to provide the specific intake of the desired constituents. In the practice of the instant invention, all of the elements of the whole liver are preserved, without chemically or otherwise alternating same. The process of the invention of course should not be compared to the above discussed prior techniques which involve extracting chemicals from liver and other foods.

It is accordingly a general object of the present invention to provide a method of processing liver to provide a highly concentrated, yet palatable and easily digested, product.

A still further object is to provide a process for treating liver so as to reduce the bulk of the liver without any loss of its essential components.

Yet another object is to provide a liver product, which in a single tablet or biscuit form, contains from between 200 to 300 micrograms of selenium and other beneficial nutrients.

A further object is to provide a novel process for freeze drying and/or dehydrating liver.

The manner in which the foregoing and other objects are achieved in accordance with the present invention will be better understood in view of the following detailed description, and accompanying method and composition embodiments, which are disclosed for illustrative purposes only.

DETAILED DESCRIPTION OF THE PREFERRED EMBODIMENT

As briefly discussed above, the present invention relates to a new and improved technique for processing liver in a manner to provide a liver product which has particular utility for use in the therapeutic treatment of certain diseases of the blood.

In accordance with the invention, the bulk of the liver material e.g., calves liver, beef liver or the like is reduced without loss of any of its essential components. This reduction of the bulk of the liver is accomplished by way of a dehydration technique which reduces the bulk of the liver without producing the unpalatable product of the prior art. In the practice of the invention the liver is first cooked in a small amount of water in a pressure vessel. The liver is cooked in this vessel for a period of time on the order from between 15 to 30 minutes at a temperature of about 212° to 235° F. or that temperature which is equivalent to about 15 to 18 pounds per square inch. In other words, the corresponding temperature which would be developed in the pressure cooker at the given pressure. After this initial cooking step, the vessel and its contents are chilled very rapidly to about 0° F. and preferably maintained at this temperature for about 20 to 60 minutes. The vessel is then evacuated by means of a suitable vacuum pump or other means as is well known in the art and held at a vacuum of approximately 15 to 28 inches of mercury for a period on the order of about 20 to 60 minutes.

The liver, which is now quite porous and substantially reduced in weight and volume, is removed from the vessel and ground into approximately rice size granules, that is, particles having a length up to about 20 millimeters and preferably in the range of from about 5 to 20 millimeters. The liver in this granular form is then placed into a high vacuum desiccator or similar apparatus wherein it is subjected to a high vacuum for an additional period of time. In this regard this vacuum should be maintained at about 24 to 29 inches of mercury for a period up from about 30 to 60 minutes. The finely divided liver is next subjected to a second grinding step wherein the particles are further reduced in size to that approximating granulated sugar crystals. Such particles preferably have an average particle size or length of from about 1 to not greater than about 5 millimeters. The finely ground liver is next spread on a tray or plate in a high vacuum chamber where it is held at about 28 to 29 inches of mercury for about 45 to 75 minutes.

The liver employed in the practice of the invention may be from any animal, as from hogs or cattle, with calves liver being particularly advantageous and thus preferred. Other meat products such as kidney may also be used. Beef liver is of course readily available and relatively inexpensive.

Turning now to more specific details of the invention and with reference to a particular advantageous embodiment and working example, the liver is first "soft" cooked in a minimum amount of water and in a pressure vessel at about 15.0 pounds per square inch (212° F.). This vessel is then rapidly chilled to 0° F. After about 30 minutes at this temperature the vessel is evacuated to about 18 inches of mercury and held at this vacuum for about 45 to 60 minutes. The liver, now quite porous and reduced in weight and volume is ground into rice size granules, having an average length not greater than about 20 milliliters. The liver is then placed into a high vacuum desiccator where it is subjected to a vacuum of about 15 to 28 inches of mercury for an additional 60 minutes. The granules, which have now been reduced in size and weight through the extraction of moisture on the order of about one percent (1%), are ground to the size of granulated sugar crystals having an average length of about 1 millimeter and not greater than about 5 millimeters.

It should be appreciated that the skill in the art, ordinary dehydration means, would not permit reduction of the moisture content to such a low content, i.e., on the order of aforesaid one percent (1%). The finely ground calves liver is next placed in a high vacuum chamber, preferably on a shallow tray, plate or like apparatus, where it is held at about 28 to 29 inches of mercury for about 60 minutes while at the same time being subjected to ultraviolet irradiation so as to produce a sterile and stable product. While the latter is optional, it is a very particularly advantageous and preferred process step.

The resulting product is now ready for encapsulation or pressing into tablets of conventional size for human consumption in a form which does not require refrigeration or vacuum packaging to prevent deterioration. The processed granules, when combined with a suitable binder, may also be pressed into tablet or biscuit form measuring approximately 1½ to 4 inches which will provide the optimum 200 to 300 micrograms daily supply of selenium and other beneficial nutrients in a highly palatable form which is easily digested. This is opposed to the rather dense, unpleasant tasting liver prepared by conventional dehydration processes. The latter also tends to suffer from the disadvantage of being very difficult to swallow.

At this point, it may be noted that in the practice of the method of the instant invention; the bulk of the raw untreated liver is reduced to about 20–35%, by weight, of its original uncooked weight. As set forth in detail hereinabove, this reduction of the bulk is effected without the loss of the liver's essential components. In this regard, it has been found that 5 ozs. of the processed liver of the invention provides the minimum daily recommended adult patient intake for therapeutic purposes. This amount would provide about 150 micrograms of selenium.

From the above it will be seen that the product of the instant invention transforms liver into a lightweight yet highly concentrated form which, in such form, may be added to other foods, especially sauces and gravies, without detection. The process of the invention is straightforward, employs conventional apparatus and/or processing equipment, and is a remarkable advance in the art. While particularly advantageous embodiments have been disclosed for illustrative purposes, it should be expressly understood that the invention is not limited thereto except as otherwise defined by the appended claims.

What is claimed is:

1. A process for producing a highly palatable liver product having a substantially reduced bulk, but without the loss of any of its essential ingredients and which, in such form, is effective for use in providing a source of said ingredients, said process comprising the steps of soft cooking the liver in a pressure vessel at a temperature between about 212° to 235° F. at about 15 pounds per square inch to 18 pounds per square inch for a period of about 15 minutes; chilling said vessel and liver to a temperature of about 0° F.; evacuating said vessel to about 18 inches of mercury and maintaining this vacuum for about 30 minutes; grinding the resulting liver into finely divided rice size granules; subjecting said rice size granules to a further vacuum treatment of about 20 inches of mercury and for a period of time of about 30 minutes; further reducing the size of said rice size granules by grinding same to finely divided particulates approximating that of granulated sugar crystals, said crystals having a length of between about 1 to 5 millimeters; subjecting said finely divided liver particulates to a high vacuum on the order of about 20 inches of mercury and for a period of about 30 minutes; and recovering the resulting product.

2. The process in accordance with claim 1 and further comprising subjecting said liver to ultra-violet irradiation to produce a sterile and stable product.

3. The process in accordance with claim 1 wherein said liver comprises calves liver.

4. The process in accordance with claim 1 wherein said liver comprises beef liver.

5. The process in accordance with claim 1 and further comprising recovering the liver product and mixing said product with a binder and pressing said mixture into biscuit form.

6. The process in accordance with claim 1 and further comprising compressing the recovered product into tablet form.

* * * * *